United States Patent [19]

Moore et al.

[11] Patent Number: 4,581,926

[45] Date of Patent: Apr. 15, 1986

[54] DETERMINATION OF STEAM QUALITY IN THERMAL INJECTION WELLS

[75] Inventors: Boyd B. Moore; Moye Wicks, III, both of Houston, Tex.

[73] Assignee: Shell Oil Company, Houston, Tex.

[21] Appl. No.: 671,657

[22] Filed: Nov. 15, 1984

[51] Int. Cl.[4] ............................................. E21B 47/00
[52] U.S. Cl. .......................................... 73/155; 73/29
[58] Field of Search ................ 73/155, 29, 30, 861.35; 166/250, 252; 374/42

[56] References Cited

U.S. PATENT DOCUMENTS

| | | | |
|---|---|---|---|
| 2,868,012 | 1/1959 | Lebourg | 73/155 |
| 3,063,292 | 11/1962 | Glenn, Jr. et al. | 73/155 |
| 3,905,226 | 9/1975 | Nicolas | 73/155 |
| 3,982,433 | 9/1976 | Stout | 73/155 |
| 4,326,411 | 4/1982 | Gant et al. | 73/155 |
| 4,409,825 | 10/1983 | Martin et al. | 73/155 |
| 4,523,479 | 6/1985 | Johnson | 73/861.35 |

Primary Examiner—Stewart J. Levy
Assistant Examiner—Robert R. Raevis

[57] ABSTRACT

A method and apparatus for measuring the quality rate of the steam injected into a hydrocarbon formation in a thermal recovery process. The method measures the density and flow rate of the steam downhole using a mechanical/electrical apparatus. The quality of the steam is calculated from the measured density and flow rate. The apparatus comprises an electric motor-generator and turbine wheel combination, the no-load speed of the motor being related to velocity of the steam while the stall torque is related to density of the steam.

14 Claims, 2 Drawing Figures

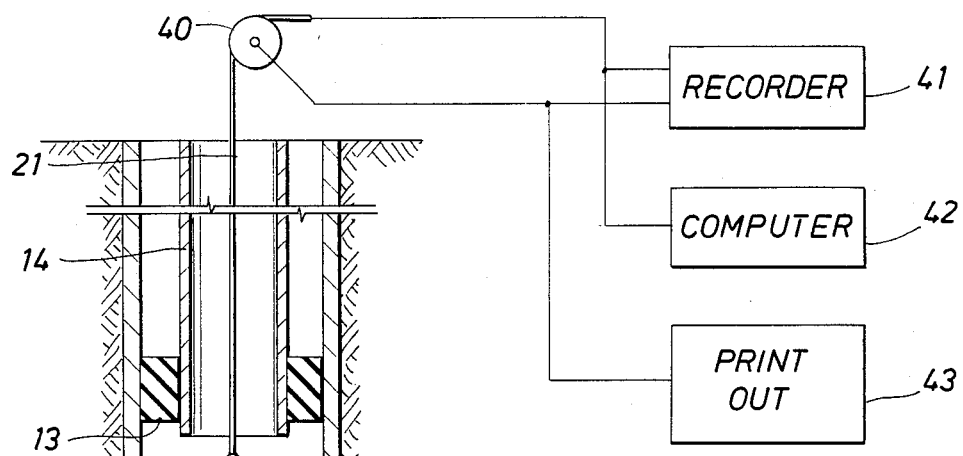
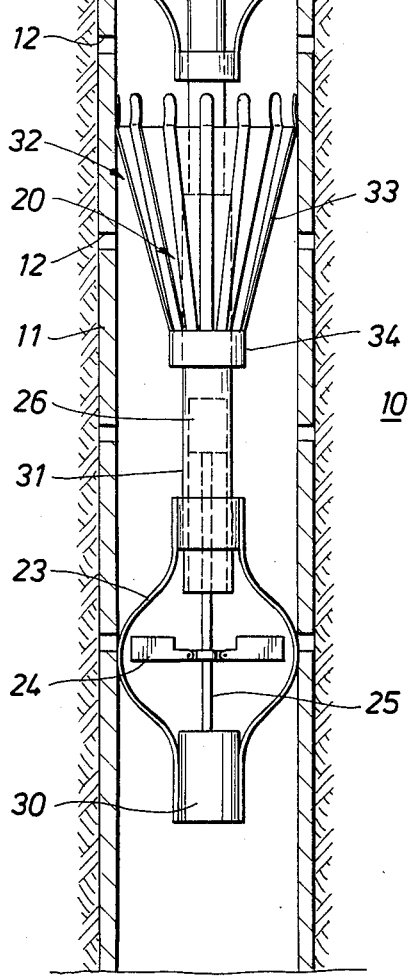
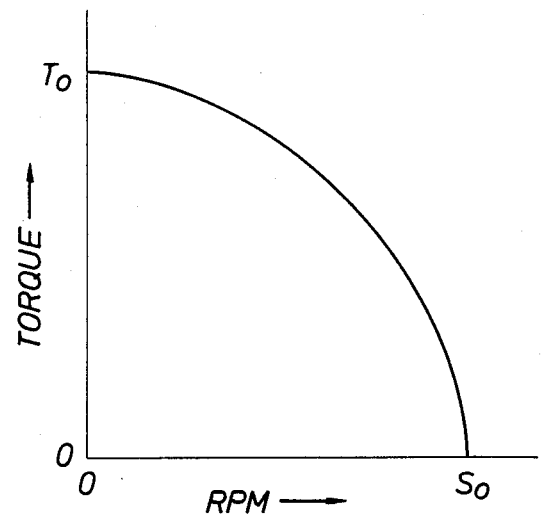

DETERMINATION OF STEAM QUALITY IN THERMAL INJECTION WELLS

BACKGROUND OF THE INVENTION

The present invention relates to the production of liquid hydrocarbons, and more particularly, to the production of liquid hydrocarbons using various thermal methods. The enhanced recovery of oil and particularly heavy crude deposits has increased during recent years as a result of decreasing reserves and increasing prices. These factors make thermal recovery methods economically attractive. In thermal recovery processes using steam, two methods are used. In the first, steam is injected into the formation for a period of time after which the well is shut in and allowed to soak. Following the soaking period, the crude oil that accumulates in the well, is produced, and the process is repeated. In the second method, the steam is used to not only heat the formation, but drive the crude toward a producing well. In both of these methods the steam flows through perforations in the well casing and it is highly desirable to know the injection profile of the steam into the formation. It is, of course, desirable that the steam enter the formation in a uniform pattern and not bypass a portion of the formation and enter only a restricted portion of the formation. It would also be desirable to know the quality of the steam being injected into each portion of the formation.

Various means have been proposed for measuring the steam quality downhole in a thermal recovery process. For example, U.S. Pat. No. 4,409,825 discloses a system for obtaining a steam sample downhole to determine the quality of the steam and dissolved solids in the sample. While this method measures the quality of the steam, it does not give a profile of the steam injection into the formation since the system does not measure steam flow. Further, the system requires the insertion of elaborate equipment in the well in addition to the installation of a separate sample tube system for conveying the steam sample to the surface. Finally, this method requires that the steam flow rate be known and it thus gives no information after the first perforation zone.

While various methods are available for measuring steam quality and flow rates in pipelines and the like, all of these methods require the use of electronic circuits for producing signals that must be transmitted to a use location. It is well known that electronic circuits will not withstand the temperatures existing in downhole steam wells, i.e. 500°-600° F. Thus, the adaption of known methods to downhole use is not possible.

BRIEF DESCRIPTION OF THE INVENTION

The present invention solves the above problems by providing an apparatus which can be lowered into a borehole to measure both the quality of the steam as well as the flow rates at various locations along the borehole. Further, the instrument does not require any electronic circuitry and thus can operate satisfactorily in thermal recovery wells.

The instrument comprises a bladed rotating member, for example, a turbine wheel, mounted on the shaft of a direct-current permanent magnet motor-generator. The motor-generator is coupled to the surface through suitable insulated conductors so that the current supplied to the motor, or the current drawn from the motor when it is operating as a generator, can be measured.

The system operates by first obtaining the no-load speed of the motor and then placing a current load on the motor until the motor stalls, at which point the stalled current of the motor is measured. From these two measurements, the torque versus speed curve can be generated and the velocity and the density of the fluid can be determined. Having the velocity and density, one can calculate the flow rate at any position along the bore-hole, as well as the quality of the steam.

BRIEF DESCRIPTION OF THE DRAWINGS

The invention will be more easily understood from the following description when taken in conjunction with the attached drawings in which:

FIG. 1 is a characteristic curve of torque versus rotational speed for a turbine.

FIG. 2 is an elevation view of the instrument installed in a borehole.

DESCRIPTION OF THE PREFERRED EMBODIMENT

The present invention is based on the laws of thermodynamics for a steady-flow system which state $$(H_2-H_1)+(V_2^2-V_1^2)/2G_c+(Z_2-Z_1)*G_1/G_c=Q-W_s \quad (1)$$

where
$H$ = enthalpy in Ft. Lb/Lb M
$V$ = average velocity in Ft./sec.
$Z$ = elevation in Ft.
$G_1$ = gravitational acceleration = 32.174 Ft./Sec.$^2$
$G_c$ = conversion factor 32.174 Lb. M Ft./Lb. Ft. Sec.$^2$
Subscripts 1 and 2 refer to upstream and downstream locations
$Q$ = heat loss between points 1 and 2, Ft. Lb./Lb. M
$W_s$ = shaft work removed from flowing stream between points 1 & 2, Ft. Lb./Lb. M When a turbine is placed in a flowing stream and if all terms are small over its length, the work which is produced is equal to the kinetic energy change across the blades. Normally, a turbine is designed to produce power and maximize the work produced, while in the present application the turbine is designed for low output in order to minimize the work produced, and hence the pressure drop across the turbine.

FIG. 1 shows the typical characteristic curve of a turbine in which rotational speed is plotted versus the torque load on the shaft. At a no-load condition, the turbine spins freely and responds as a turbine meter. Thus, the following expression describes the turbine's operation:

$$I\ V\alpha S_o \quad (2)$$

where
$V$ = fluid velocity in Ft./Sec.
$S_o$ = rotational speed in RPM.

After obtaining the no-load speed of the turbine an electrical current is supplied from the surface to overcome the current produced by the motor-generator and to cause it to slow down. A series of measurements of current flow and speed are made to obtain the torque versus speed curve shown in FIG. 1. The no-load speed and stall torque can be accurately determined from the torque versus speed curve. This eliminates the problems of trying to measure no-load speed and stall torque. As the motor-generator slows down it behaves like a dragbody and the lift force tending to cause the rotation of the blades is directly proportional to the kinetic energy, which can be expressed as follows:

$$\rho * V^2 \alpha T_o \tag{3}$$

where
$\rho$ = density of mixture in Lb./Ft.$^3$
$T_o$ = stall torque

The above expressions provide two equations for the two unknown quantities $\rho$ and V, from which one can develop the following expressions which will provide the steam quality X and the flow rate W at the location of the turbine.

$$1/\rho = (1-X)/\rho_1 + (X)/\rho_g \tag{4}$$

where
X = steam quality, weight fraction
$\rho$ = density of the liquid/vapor mixture, in Lb./Ft$^3$
$\rho_1$ = density of liquid, in Lb./Ft$^3$
$\rho_g$ = density of vapor, in Lb./Ft$^3$ $$W = \rho * V * A \tag{5}$$

W = mass flow rate of the liquid/vapor mixture in Lb/Sec.
V = average velocity of the liquid/vapor mixture, in Ft/Sec.
A = flow area in Ft$^2$ Referring to FIG. 2, there is shown an implement limitation of the above ideas which can be used to measure two-phase steam flow in a thermal well. Although the description relates to the use of the apparatus to measure two-phase steam flow in a thermal well, it can obviously be adapted to measure any two-phase flow.

Referring to FIG. 2, there is shown a formation 10 having a borehole extending therethrough which is cased by the casing 11. The casing is provided with a series of perforations 12 through which the steam can be injected into the formation. The steam is transported from the surface to the formation by means of a tubing string 14 which extends into the cased hole while packer 13 isolates the perforated part of the casing from the remainder of the casing. The apparatus consists of a downhole sonde 20 which is lowered into a borehole through the tubing string by means of a flexible conduit 21. The conduit 21, in addition to having the strength to support the sonde and raise and lower it in the borehole, also includes the electrical circuits required to transmit power to or from the motor. The conduit 21 is preferably a high temperature armored cable. For example, it may comprise a stainless steel pressure tube in which electrical conductors having high temperature insulation are disposed. In addition, the stainless tube can be hermetically sealed to isolate the electrical conductors from the steam and well fluids. A pair of bow springs 22 and 23 are provided on the sonde for centering the sonde in the casing. The turbine wheel 24 is mounted on the motor shaft 25, while the motor-generator 26 is disposed in the sonde. The lower end of the motor shaft is supported by a pivot bearing carried in the bottom member 30 of the sonde. The turbine blades are pivoted at their inner ends by pivot pins and are designed to be folded down so that the sonde can be withdrawn from the casing into the tubing and thus from the borehole. To assist in folding the blades, an outer member 31 slides on the outer surface of the sonde and forces the blades downwardly and inwardly when the sonde is withdrawn from the borehole. The motor-generator should incorporate some means for producing a signal related to its rotating speed. For example, a magnet may be mounted on the motor shaft and a detector coil mounted in the housing to produce an alternating current signal whose frequency will be equal to the motor-generator speed.

It is desirable to incorporate a means in the logging sonde to remove water from the wall of the casing 11 and mix it with the two-phase flow in the center. A suitable means would be a metal petal basket 32, manufactured by Baker Oil Tools of Houston, Tex. This type of device comprises a plurality of metal petals fingers 33 mounted on a ring 34. The fingers are retracted to insert the basket in a borehole and then expanded to form a funnel when the basket is in place. In the expanded position the basket will cause the water flowing along the wall of the casing to flow to the center of the casing where it will mix with the two-phase flow. Other devices can also be used to ensure that water is removed from the casing wall and recombined with the two-phase flow. This will ensure that quality and flow measurements accurately represent the true conditions in the borehole.

At the surface, the conduit 21 passes over a measuring sheave 40 and is connected to the recorder 41 and a computer 42. The measuring sheave is also connected to the recorder 41 and a print-out device 43 so that the recorded or displayed data can be correlated with the depth of the sonde in the borehole. The recorder can be a conventional digital recorder which accepts the current signal on the conductors and converts it to a related digital number which is recorded. The computer 42 can be programmed to control the operational sequence of the downhole motor, and in addition, compute the flow rate and quality of the steam flowing at various locations in the borehole. The calculations to determine the flow rate and quality of steam are described in greater detail below.

It can be shown that the current at stalled conditions can be converted to torque in Ft./Lbs., by the following expression:

$$T_o = K \cdot I \tag{6}$$

where
I = current in amps
K = Z*p*$\Phi$/(2 *a)
where
Z = number of inductors
p = number of poles
$\Phi$ = magnetic flux in Weber's
a = number of parallel paths through the armature Having the torque in Ft./Lbs., one can determine the lift force on the blades from the following expression:

$$F_1 = T_o/R \tag{7}$$

where
$F_1$ = lift force in Lbs.
R = radius of the motor shaft in Ft.

Using the lift force, one can then compute the density of the mixture from the following expression:

$$\rho * V^2 = F_1 * 2 G_c/(C_L A_p) \tag{8}$$

where
$\rho$ = density of mixture in Lbs./Ft$^3$
V = flow velocity in Ft./Sec.

$C_L$ = lift coefficient
$A_p$ = projected area of turbine blades in Ft$^2$
$G_c$ = conversion factor—32.174 Lbs M Ft/Sec$^2$ Knowing the density of the mixture and the density of water and steam under the temperature and pressure conditions existing in the well, one can calculate the quality of the steam from the following expression:

Density of the mixture = (1−X)* the density of the water + X* the density of the vapor
where X = steam quality.

The temperature and pressure of the steam can be measured at the surface of the well and at any position in the well by conventional means. The density of the liquid and vapor phases can then be obtained from conventional steam tables. Most steam thermal recovery projects use wet steam and it is only necessary to measure either the temperature or the pressure in order to determine the density of the liquid and vapor phase assuming thermodynamic equilibrium exists.

From the above description, it is seen that having the free rotational speed of the turbine and the current required to stall the turbine, one can calculate both the flow rate and steam quality at the position of the turbine in the borehole. The calculations for flow rate and steam quality can obviously be programmed in the computer 41 so that the measurements can be converted directly to flow rates and steam quality at the well site.

The lift coefficient appearing in Equation 8 can be obtained by calibrating the instrument under known conditions. Once calibrated, the lift coefficient will remain constant over the range of steam conditions existing in thermal recovery wells. This can be a simple calibration at the surface of the well, or a laboratory calculation.

What is claimed is:

1. A method for determining the quality of the steam being injected into a hydrocarbon bearing formation surrounding a well in a thermal recovery process, said method comprising:
   positioning a bladed rotating member downhole;
   measuring the free rotational speed $S_o$ of the rotating member;
   measuring the torque $T_o$ required to stall the rotating member;
   determining the density of the liquid and vapor phases of the steam;
   determining the density $\rho$ of the steam from the expression $T_o = K*V^2*\rho$ where K is a proportionality constant for a particular rotating member and V is the flow velocity of the steam; and
   determining the steam quality using the density $\rho$ and the density of the liquid and vapor phases.

2. The method of claim 1 wherein said bladed member is coupled to a direct current motor-generator and the energy required to stall said bladed member is determined by measuring the current flow when said motor-generator is stalled.

3. The method of claim 2 wherein the torque under stall conditions is determined from the expression $$T = K \times I$$

where
   T = the torque in dyne/cm
   I = current flow in amps
   K = Z*p*Φ/(2 *a)
   Z = number of inductors
   p = number of poles
   Φ = magnetic flux in Weber
   a = number of parallel paths through the armature.

4. The method of claim 3 wherein the lift force $F_1$ on the bladed member is determined from the expression $$F_1 = T_o/R$$

where
   $T_o$ = stall torque
   R = shaft radius.

5. The method of claim 4 wherein the density $\rho$ of the two-phase mixture is determined from the expression $$\rho*V^2 = F_1*2G_c/(C_L A_p)$$

where
   V = flow velocity in Ft/Sec
   $C_L$ = lift coefficient (a constant determined from calibration tests)
   $A_p$ = projected area of blades in Ft$^2$
   $G_c$ = conversion factor = 32.174 Lb M Ft/Lb.f Sec$^2$.

6. An apparatus for determining the density of a two-phase flow of liquid and vapor comprising:
   a direct current motor-generator;
   a rotating member having at least one blade, said rotating member being secured to the shaft of said motor-generator;
   circuit means coupled to said motor-generator to both supply electrical power to the motor-generator and measure the rotational speed of the motor-generator; and
   means for mounting said motor-generator and rotating member in the two-phase flow to determine the speed versus load characteristics of the motor-generator.

7. The apparatus of claim 6 wherein said circuit means includes means for varying the electric load on said motor-generator to stall and motor-generator and measure the current flow under said stall condition.

8. The apparatus of claim 7 and in addition a logging sonde, said motor-generator and rotating member being mounted in said sonde to permit said sonde to be lowered into a borehole.

9. The apparatus of claim 8 and in addition means mounted on said sonde to centralize the sonde in a borehole.

10. The apparatus of claim 9 and in addition means mounted on said sonde for providing a uniform mixture of both phases of the two-phase flow to said rotating member.

11. The apparatus of claim 6 wherein said motor-generator and rotating member are designed for low output.

12. The apparatus of claim 6 and in addition means for retracting said at least one blade.

13. A method for measuring two-phase flow and determining the percentage of each phase, said method comprising:
   positioning a combination rotating and drag member in the two-phase flow;
   measuring the free rotational speed of the member and the torque produced by the member at zero rotational speed;
   converting the measured rotation to velocity value;
   converting the measured torque to density value; and
   using the velocity and density values to determine the flow rate and percent of each phase in the two-phase flow.

14. The method of claim 13 wherein said measured rotation is converted to velocity using the expression $$S_o KV$$

where
 $S_o$ = rotational speed
 V = velocity
 K = a constant.

* * * * *